United States Patent
Sul

(10) Patent No.: US 7,452,566 B2
(45) Date of Patent: Nov. 18, 2008

(54) OSSEOINDUCTIVE MAGNESIUM-TITANATE IMPLANT AND METHOD OF MANUFACTURING THE SAME

(76) Inventor: Young-Taek Sul, Department of Biomaterials Sciences, Göteborg University, Box 412, SE 405 30 Göteborg (SE)

( * ) Notice: Subject to any disclaimer, the term of this patent is extended or adjusted under 35 U.S.C. 154(b) by 9 days.

(21) Appl. No.: 10/562,925

(22) PCT Filed: Mar. 4, 2004

(86) PCT No.: PCT/KR2004/000460

§ 371 (c)(1), (2), (4) Date: Dec. 30, 2005

(87) PCT Pub. No.: WO2005/084577

PCT Pub. Date: Sep. 15, 2005

(65) Prior Publication Data

US 2006/0161263 A1     Jul. 20, 2006

(51) Int. Cl.
  *A61K 6/00*    (2006.01)
  *A61C 8/00*    (2006.01)
(52) U.S. Cl. .................. 427/2.26; 205/322; 427/2.24; 433/201.1
(58) Field of Classification Search ........... 205/322; 427/2.24, 2.26; 428/304.3, 469, 472, 640, 428/701, 702; 433/201.1; 623/23.53, 23.55, 623/901
See application file for complete search history.

(56) References Cited

U.S. PATENT DOCUMENTS 5,383,935 A    1/1995   Shirkhanzadeh

FOREIGN PATENT DOCUMENTS

| DE | 2135004 A | * | 1/1973 |
| DE | 4407993 | | 9/1995 |
| EP | 676179 | | 5/2000 |
| JP | 2003-268481 | | 9/2003 |
| KR | 2004-46248 | | 6/2004 |
| WO | WO 00/72777 A1 | * | 7/2000 |

OTHER PUBLICATIONS

Abstract of KR9208348 B to Chang et al., Sep. 1992.*
Computer translation of JP2003-268481.*

* cited by examiner

*Primary Examiner*—John J. Zimmerman
*Assistant Examiner*—Aaron Austin
(74) *Attorney, Agent, or Firm*—Robert E. Bushnell, Esq.

(57) ABSTRACT

A magnesium titanate oxide film implant, and a method for preparing the same. The magnesium titanate oxide film implant is prepared by forming a titanium oxide film (a magnesium titanate oxide film) in which magnesium is incorporated into the surface of titanium or a titanium alloy. A magnesium titanate oxide film implant is prepared by irradiating UV light on an implant body made of titanium or a titanium alloy in distilled water, dipping the UV light-irradiated implant body in an electrolyte solution containing magnesium, and coating a magnesium titanate oxide film on the dipped implant body by anodic oxidation. Therefore, the present invention can provide an implant having increased bioactivity of a titanium oxide film formed by anodic oxidation, and provides an optimum magnesium titanate oxide ($Ti_xMg_yO_z$) thickness for successful osseointegration of the magnesium titanate ($Ti_xMg_yO_z$) implant.

7 Claims, 6 Drawing Sheets

\*: barrier oxide layer

OSSEOINDUCTIVE MAGNESIUM-TITANATE IMPLANT AND METHOD OF MANUFACTURING THE SAME

CLAIM OF PRIORITY

This application makes reference to, incorporates the same herein, and claims all benefits accruing under Title 35 U.S. Code §365(b)(c) of my PCT International application entitled OSSEOINDUCTIVE MAGNESIUM-TITANATE IMPLANT AND METHOD OF MANUFACTURING THE SAME, filed on 4 Mar. 2004 and duly assigned Ser. No. PCT/KR2004/000460.

TECHNICAL FIELD

The present invention relates to a magnesium titanate oxide film implant for insertion into a living body, utilized in medical fields such as dentistry, orthopedic surgery, maxillofacial surgery and plastic surgery, and a method for preparing the same.

BACKGROUND ART

Generally, titanium (or titanium alloy) implants are subjected to a variety of surface treatments to improve biocompatibility thereof following lathe processing and milling. As examples of such surface treatment methods, mention may be made of etching in acidic/alkaline solutions, particle blasting, plasma spray, thermal oxidation, sol-gel induced coating using bioactive materials such as hydroxyapatite, bioglass and bioceramics, physical/chemical vapor deposition, Ion Implantation or Plasma Source Ion Implantation, electrochemical anodic oxidation and applied techniques using any combination thereof.

As examples of surface treatment methods using the electrochemical anodic oxidation among those methods, there are known a method for preparing an oxide film using a mixed solution of sulfuric acid and hydrochloric acid, or sulfuric acid and phosphoric acid, or phosphoric acid and oxalic acid (German Patent No. 2,216,432, Japanese Patent Publication Laid-Open No. Hei 02-194,195, Swedish Patent No. 1999-01973), a method for preparing an oxide film containing calcium and phosphorus (U.S. Pat. No. 5,478,237), a method involving forming an anodized film, followed by heat treatment (U.S. Pat. No. 5,354,390), a method involving forming calcium-phosphate using anodic oxidation, followed by heat of hydration treatment so as to prepare hydroxyapatite (U.S. Pat. No. 5,354,390), a method for preparing dicalcium phosphate anhydrous (DCPA, CaHPO), tricalcium phosphate (alpha-TCP), amorphous calcium phosphate (ACP) and dicalcium phosphate dihydrate (DCPD) (U.S. Pat. No. 5,997,62), using anodic oxidation, and a method for preparing a titanium oxide film by anodic oxidation (EP Patent Publication No. 0 676 179).

However, implants in which titanium or titanium alloy was coated with the above-mentioned calcium-phosphate or hydroxyapatite, have suffered from delamination of coated materials, or biodegradation and resorption due to biological actions at interfaces between an implant body and coating materials or inside coating materials, thus causing chronic inflammation of bone tissue in the vicinity of the implant, and thereby prolonged use thereof may result in continuous drop of a success rate. Further, the thicker the oxide film is, the lower the mechanical strength of the oxide film is, and the oxide film may be delaminated into bone tissue from the interface between the implant and bone tissue.

DISCLOSURE

Technical Problem

Therefore, the present invention has been made in view of the above problems, and it is an object of the present invention to provide a magnesium titanate oxide film implant having increased biocompatibility and bioactivity of a titanium oxide film formed by anodic oxidation, and a process for preparing the same.

It is another object of the present invention to provide a magnesium titanate oxide film implant, by forming an oxide film having osseoinductive properties and excellent mechanical strength on surfaces of titanium and titanium alloy implants, which are utilized in dentistry, orthopedic surgery, otorhinolaryngology, maxillofacial surgery and plastic surgery, so as to induce rapid and strong bone binding, thereby leading to successful osseointegration; and a method for preparing the same.

Technical Solution

In accordance with an aspect of the present invention, the above and other objects can be accomplished by the provision of a magnesium titanate oxide film implant, comprising:
   an implant body containing titanium or a titanium alloy; and
   a magnesium titanate oxide film formed on the surface of the body.

In the present invention, the magnesium titanate oxide film is prepared by low voltage dielectric breakdown anodic oxidation. Preferably, the magnesium titanate oxide film contains 6 to 26% of titanium, 51 to 71% of oxygen and 1.8 to 32% of magnesium, as main ingredients; 6 to 15% of carbon, 0.3 to 6% of phosphorus, 0.3 to 2.1% of sodium and 1 to 2% of nitrogen, as minor ingredients; and, sulfur, calcium and potassium in an amount of less than 1%, as additives.

In accordance with another aspect of the present invention, there is provided a process for preparing a magnesium titanate oxide film implant, comprising:
   irradiating UV light on an implant body made of titanium or a titanium alloy in distilled water for more than 2 hours;
   dipping the UV light-irradiated implant body in an electrolyte solution containing magnesium; and
   coating a magnesium titanate oxide film on the dipped implant body by anodic oxidation at a voltage of 60 to 500V.

Now, a magnesium titanate oxide film implant in accordance with the present invention and a process for preparing the same will be described in detail with reference to the accompanying drawings.

The magnesium titanate oxide film implant in accordance with the present invention is composed of an implant body and a magnesium titanate oxide film formed on the surface of the implant body. The implant body used in the present invention is made of titanium or a titanium alloy. The magnesium titanate oxide film is formed by incorporating magnesium into the oxide film of the implant at low voltage by dielectric breakdown anodic oxidation, and preferably, contains 1.8 to 50% of magnesium, 6 to 26% of titanium and 51 to 71% of oxygen in an atomic ratio, as main ingredients, and optionally, may further contain 6 to 15% of carbon, 0.3 to 6% of phosphorus, 0.3 to 2.1% of sodium, 1 to 2% of nitrogen, and trace amounts of sulfur, calcium and potassium. Additionally, the magnesium titanate oxide film has a bilayer structure including an upper porous layer and a lower barrier oxide layer. The magnesium titanate oxide film preferably has a thickness of 300 nm to 30 μm, and more preferably 500 nm to 10 μm.

The biochemical action mechanism of the magnesium titanate oxide film implant having such a constitution is as follows. The magnesium titanate oxide film implant further includes magnesium in the chemical composition of a titanium oxide film, and thus, induces rapid and strong biochemical binding between the implant and bone tissue. $Mg^{2+}$ ions migrate to the outermost layer of the implant or migrate into bodily fluids so as to cause an ion exchange reaction with $Ca^{2+}$ ions present in the bodily fluids, thus resulting in migration of ions. As a result, the implant surface is electrostatically bound to bone matrix proteins having polyanionic properties, such as collagen type 1, thrombospondins, fibronectin, vitronectin, fibrillin, osteoadherin, osteopontin, bone sialoprotein, osteocalcin, osteonectin and BAG-75. Such electrostatic binding between the implant and bone matrix proteins serially promotes biomineralization around the implant. Further, the implant in accordance with the present invention has a porous magnesium titanate surface and in turn, induces ingrowth of bone tissue into surface pores, thereby inducing a strong mechanical binding between the implant and bone tissue. That is, the porous magnesium titanate oxide film has osseoinductive surface properties and thus the resulting synergistic effects of biochemical and mechanical binding between the implant and bone tissue produces rapid and strong osseointegration.

Next, a process for preparing a magnesium titanate oxide film implant in accordance with the present invention will be described.

The process for preparing a magnesium titanate oxide film implant in accordance with the present invention comprises the steps of: irradiating UV light on an implant body in distilled water for more than 2 hours; dipping the UV light-irradiated implant body in an electrolyte solution containing magnesium; and coating a magnesium titanate oxide film on the dipped implant body by anodic oxidation.

Specifically, details are provided on respective steps for the above-mentioned process. The implant body is first washed and rinsed with suitable agents such as alcohols to degrease and then UV light is irradiated on the implant body in distilled water, for more than 2 hours. Irradiation of UV light on the implant body in distilled water for more than 2 hours is a technique affecting implantation of metal ions in anodic oxidation constituting the present invention.

Then, the implant body thus irradiated is dipped in a magnesium-containing solution. The solution constituting the present invention is able to form a magnesium-containing titanium oxide film (a magnesium titanate oxide film, $Ti_xMg_yO_z$) by low voltage dielectric breakdown anodic oxidation in accordance with the present invention, in any single or mixed solution containing magnesium, such as magnesium acetate, magnesium phosphate, magnesium sulphate, magnesium iodate, magnesium gluconate, magnesium nitrate, magnesium hydroxide and magnesium chloride. In addition, the magnesium titanate oxide film in accordance with the present invention preferably maintains magnesium content in a range of 1 to 35%. For this purpose, a composition ratio of the above-mentioned compounds in the solution may vary. Further, in order to adjust a pH of any single or mixed solution containing magnesium, there may be added sulfuric acid, phosphoric acid, various organic acids, for example, acetic acid, oxalic acid, malic acid, succinic acid, malonic acid, and boric acid, sodium hydroxide or potassium hydroxide as a buffering agent.

Next, using the implant as the positive electrode and platinum as the negative electrode, a magnesium titanate oxide film is formed on the surface of the implant by inducing microarc on the positive electrode surface thereof at a low voltage of about 60 to 500 V. Although a mechanism of forming the magnesium titanate oxide film is not fully known, it is believed that magnesium ions or magnesium complex ion compounds undergo colloidal deposition by a driving force of electric field.

The magnesium titanate oxide film in accordance with the present invention provides creative and exclusive chemical constitution, differing from a conventional oxide film implant. FIGS. 1 and 2 are electron micrographs of an osseoinductive magnesium titanate oxide film implant after anodic oxidation in accordance with the present invention, respectively. FIG. 1 is an electron micrograph of the surface of an osseoinductive magnesium titanate oxide film, and FIG. 2 is a longitudinal cross-sectional view of the surface of the osseoinductive magnesium titanate oxide film implant. As shown in FIG. 1, since the surface of the magnesium titanate oxide film has a porous magnesium titanate surface, it may induce ingrowth of bone tissue into those pores, thereby resulting in a strong mechanical binding between the implant and bone tissue. As shown in FIG. 2, the osseoinductive magnesium titanate oxide film implant in accordance with the present invention comprise of an implant body 1 made up of titanium or a titanium alloy and magnesium titanate oxide films 2 and 3, the magnesium titanate oxide film being further divided into the surface porous oxide layer 3 and a barrier oxide layer 2 formed between the surface and implant body.

In addition, in order to ensure prolonged and successful function of the implant in vivo, the oxide film should have excellent mechanical properties (for example, compressive strength and tensile strength). In order to structurally reinforce mechanical properties of the titanium oxide film containing magnesium, the present invention increases current density up to 4,000 $mA/cm^2$, when performing anodic oxidation. Increasing current density increases the growth rate of the barrier oxide layer on the implant surface, and the thickness of the lower barrier oxide layer 2 becomes relatively thicker, as compared to that of the surface porous oxide layer 3. As a result, the magnesium titanate oxide film in accordance with the present invention has structural characteristics which are more highly resistant to external forces, as compared to the conventional oxide film implant in which the entire oxide film is filled with pores or channels.

Further, as another method of increasing the growth rate of the titanium oxide film containing magnesium, the temperature of the solution is kept within 30° C. as much as possible.

Meanwhile, the thicker the oxide film is, the lower the mechanical strength such as tensile strength and compressive strength of the oxide film is, and thus, the titanate oxide film may be delaminated into bone tissue from the interface between the implant and bone tissue. The present invention provides optimized magnesium titanate oxide ($Ti_xMg_yO_z$) thickness to effect successful osseointegration of the magnesium titanate oxide film implant. In order to accomplish this, at the same time, the present invention provides voltage (ranging from 60 to 500V) producing the corresponding optimized thickness formation of the oxide film.

Additionally, in order to prevent weakening of mechanical strength of the magnesium titanate oxide film due to chemical and structural defects thereof resulting from capture of gas (largely, $O_2$, $H_2$), which is produced in the course of a low voltage dielectric breakdown anodic oxidation process, on the positive electrode surface of the implant, agitation rate of a stirrer is maintained at more than 500 rpm to minimize gas adsorption on the positive electrode surface of the implant.

Osseoinductive surface properties such as magnesium content and surface processibility, shape of the surface, and thickness of the oxide film in the magnesium titanate oxide film may vary depending on various factors such as the composition ratio of the solution, applied voltage, current density, solution temperature, agitation rate and pH. Except for these properties, the magnesium titanate oxide film in accordance with the present invention can be formed by using any conventional anodic oxidation methods and apparatuses.

Advantageous Effects

The present invention provides an optimum thickness of the magnesium titanate oxide film ($Ti_xMg_yO_z$) to effect best successful osseointegration of a magnesium titanate ($Ti_xMg_yO_z$) implant. The porous magnesium titanate oxide film ($Ti_xMg_yO_z$) in accordance with the present invention has creative and exclusive osseoinductive surface properties, differing from conventional oxide film implants. In particular, incorporation of magnesium into the chemical composition of the implant oxide film induces rapid osseointegration by biochemical binding with bone tissue (biochemical osseointegration). Also, the porous surface structure of the oxide film induces attachment of bone matrix proteins and ingrowth of bone tissue into the pores, and thereby provides opportunities to reinforce mechanical osseointegration with the implant (mechanical osseointegration). As a result, the porous magnesium titanate oxide film implant induces rapid and strong osseointegration due to the resulting synergistic effects of biochemical binding and mechanical binding between the implant and bone tissue, and thereby improves, on a long-term basis, functionality and success rate of the titanium and titanium alloy implants, in areas such as dentistry, orthopedic surgery, otorhinolaryngology, maxillofacial surgery and plastic surgery, so as to induce rapid and strong bone binding, thereby leading to successful osseointegration.

DESCRIPTION OF DRAWINGS

The above and other objects, features and other advantages of the present invention will be more clearly understood from the following detailed description taken in conjunction with the accompanying drawings, in which.

Best Mode

Figure 1:
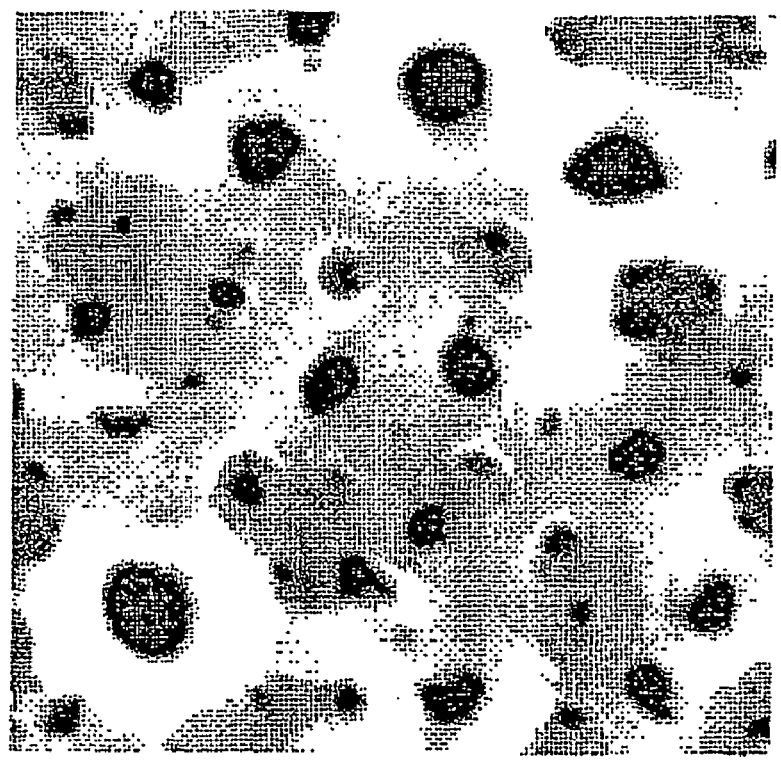
FIG. 1 is an electron micrograph of the surface of an osseoinductive magnesium titanate oxide film implant in accordance with the present invention.
Figure 2:
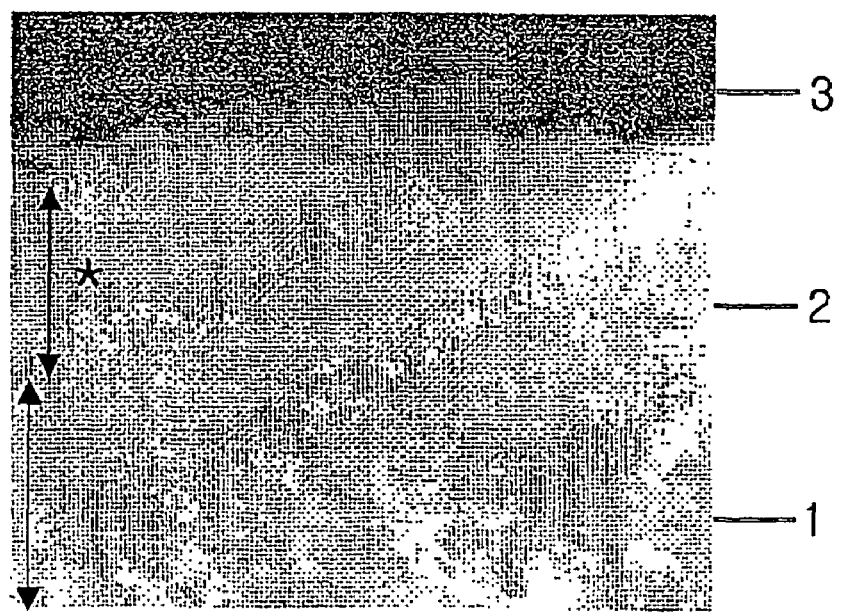
FIG. 2 is a longitudinal cross-sectional view of the surface of an osseoinductive magnesium titanate oxide film implant in accordance with the present invention.
Figure 3:
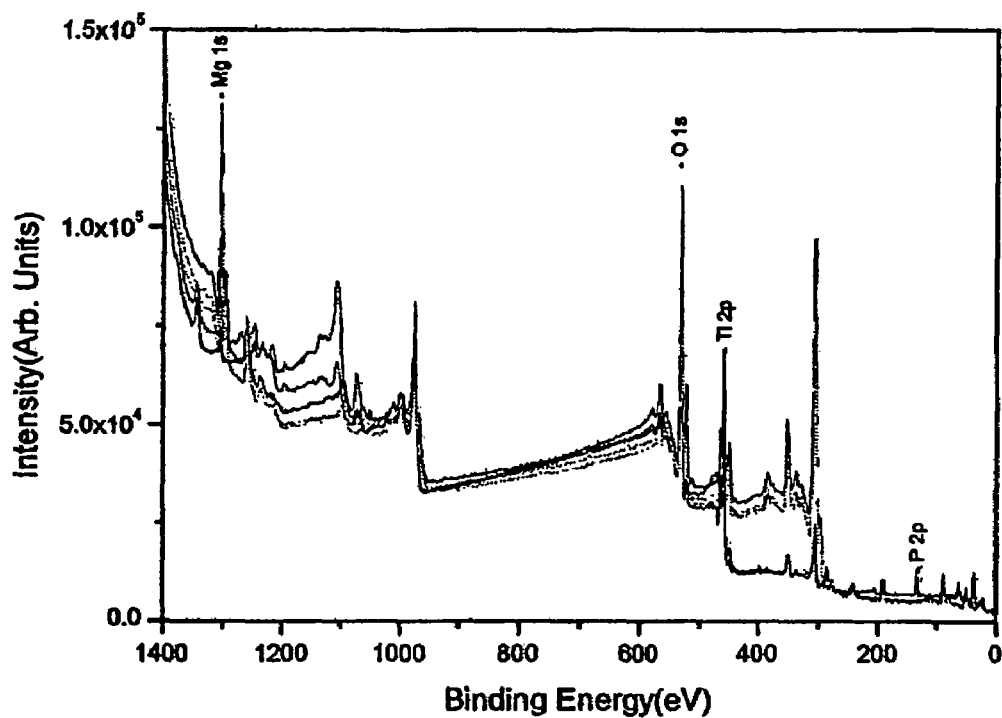
FIG. 3 shows results of qualitative analysis of a magnesium titanate oxide film in accordance with the present invention, by XPS analysis.
Figure 4:
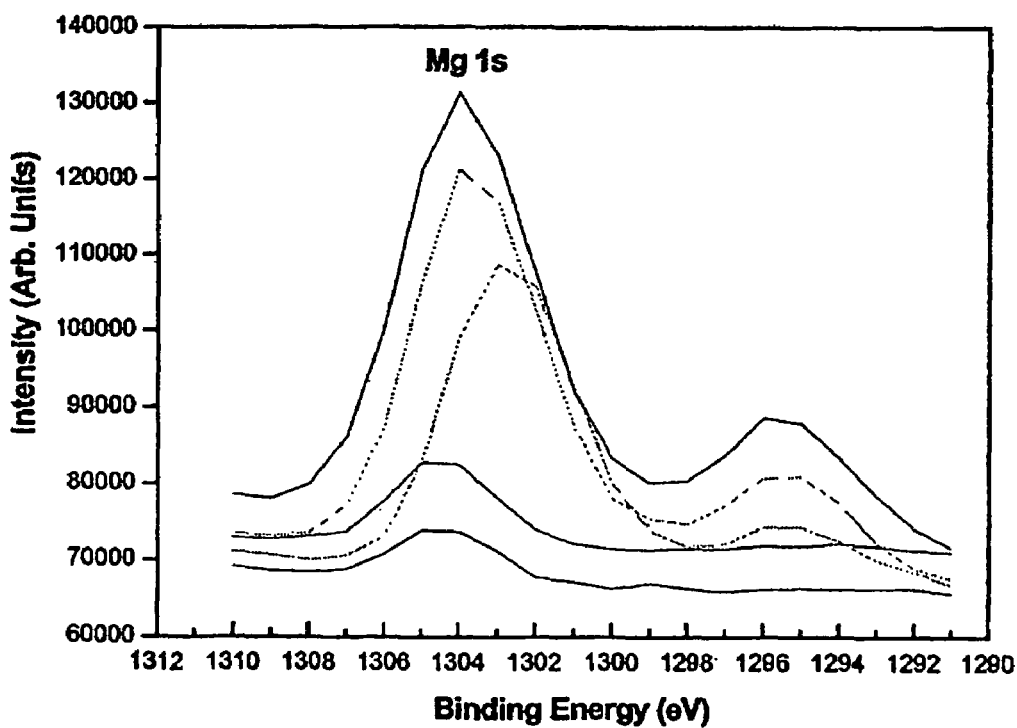
FIG. 4 shows results of qualitative analysis of Mg, among constituents of a magnesium titanate oxide film in accordance with the present invention, by XPS analysis.
Figure 5:
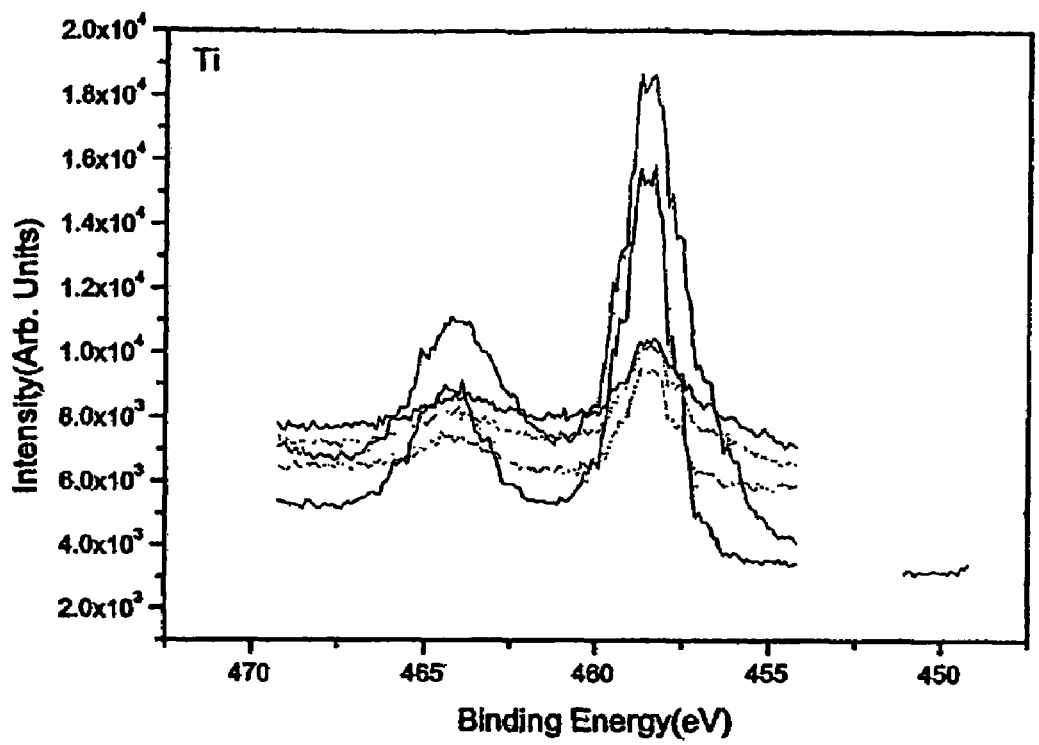
FIG. 5 shows results of a qualitative analysis of Ti, among constituents of a magnesium titanate oxide film in accordance with the present invention, by XPS analysis.
Figure 6:
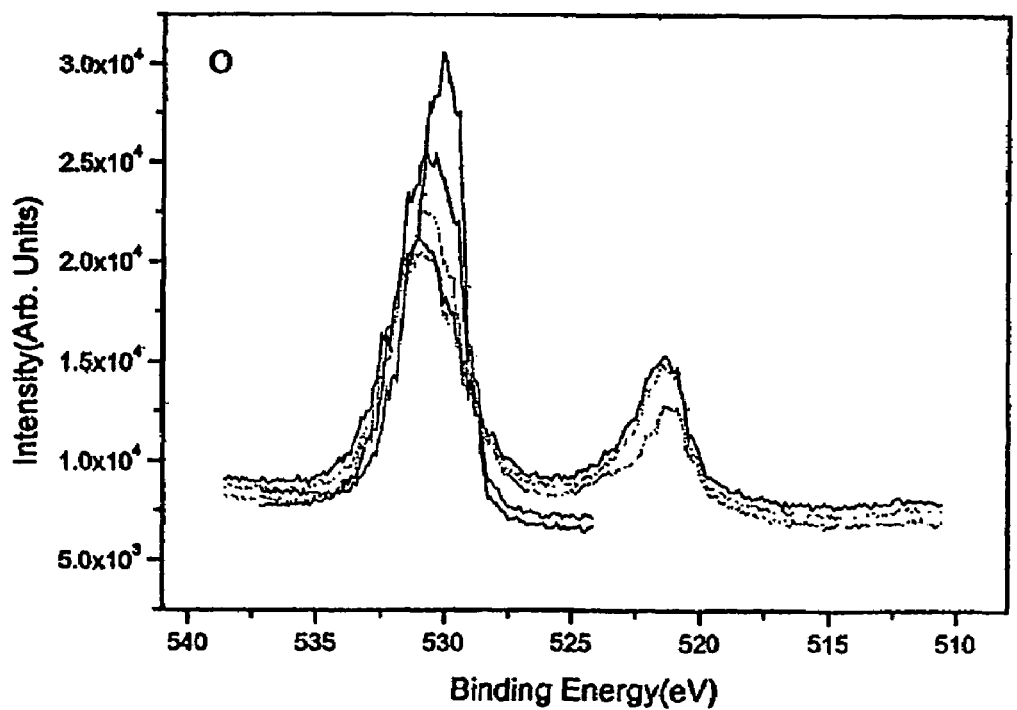
FIG. 6 shows results of qualitative analysis of O, among constituents of a magnesium titanate oxide film in accordance with the present invention, by XPS analysis.

Now, preferred embodiments of a magnesium titanate oxide film implant in accordance with the present invention and a process for preparing the same will be described in detail.

Using high resolution surface analysis instruments such as X-ray Photoelectron Spectroscopes(XPS), Auger Electron Spectroscopes (AES), Scanning Electron Microscopes (SEM), Transmission Electron Microscopes (TEM) and X-ray Diffraction (XRD), the present invention performs qualitative or quantitative characterization of osseoinductive surface properties of magnesium titanate of the above-mentioned titanium/titanium alloy implant, such as a chemical composition of magnesium titanate ($Ti_xMg_yO_z$), a thickness of magnesium titanate, pore configurations thereof, shape and structure of surface and longitudinal cross-section of magnesium titanate and crystallinity thereof. Specific experimental conditions are presented in the following Examples. These examples are provided only for illustrating the present invention and should not be construed as limiting the scope and sprit of the present invention.

Mode for Invention

EXAMPLES

In accordance with Examples of the present invention, as an electrolyte solution for forming a magnesium titanate oxide film, 0.01 M to 1.0 M magnesium acetate, magnesium phosphate, magnesium sulphate, magnesium iodate, magnesium gluconate, magnesium nitrate, magnesium hydroxide, magnesium chloride or ethylenediamine tetraacetic acid was used alone or in any mixed solution thereof. Further, in order to adjust pH of a single or mixed solution to a range between 3.0 and 12.5, sulfuric acid, phosphoric acid, or various organic acids, for example, acetic acid, oxalic acid, malic acid, succinic acid, malonic acid, or boric acid was further added. In addition, a buffering agent such as sodium hydroxide or potassium hydroxide was added. Where such buffering agent was added, the total concentration of the electrolyte solution increased up to 20 M.

In accordance with Examples of the present invention, current density of the electrolyte solution containing magnesium was set to a range of between 10 and 4000 mA. Additionally, in accordance with Examples of the present invention, voltage for performing anodic oxidation was variously set within a range of between DC 23 to 500V. Further, in order to prevent chemical and/or structural weakening of mechanical strength of the magnesium titanate oxide film in accordance with Examples of the present invention, agitation rate was maintained above 500 rpm and the solution temperature was kept below 30° C. Briefly, experimental conditions for the above-mentioned examples are shown in Table 1 below.

TABLE 1

| Ref. No. | Ingredients of Electrolyte Solution | Concentration of Electrolyte Solution (Mol/l) | Current Density (mA/cm$^2$) | Voltage (V, DC) | pH |
| --- | --- | --- | --- | --- | --- |
| 1 | Magnesium acetate + buffering agent | 0.01-1.0 | 30-4000 | 50-500 | Below 7.0 |
| 2 | Magnesium phosphate + buffering agent | 0.01-1.0 | 30-4000 | 50-500 | Below 7.0 |

TABLE 1-continued

| Ref. No. | Ingredients of Electrolyte Solution | Concentration of Electrolyte Solution (Mol/l) | Current Density (mA/cm$^2$) | Voltage (V, DC) | pH |
|---|---|---|---|---|---|
| 3 | Magnesium sulphate + buffering agent | 0.01-1.0 | 30-4000 | 50-500 | Below 7.0 |
| 4 | Magnesium iodate + buffering agent | 0.01-1.0 | 120-1000 | 50-500 | Below 7.0 |
| 5 | Magnesium gluconate + buffering agent | 0.01-1.0 | 60-4000 | 50-500 | Below 7.0 |
| 6 | Magnesium nitrate + buffering agent | 0.01-1.0 | 10-300 | 23-500 | Below 7.0 |
| 7 | Magnesium hydroxide + buffering agent | 0.01-1.0 | 30-4000 | 50-500 | Below 7.0 |
| 8 | Magnesium chloride + buffering agent | 0.01-1.0 | 30-4000 | 50-500 | Below 7.0 |
| 9 | Magnesium nitrate + acetic acid + buffering agent | 0.01-1.0 | 30-2000 | 23-500 | 3.5-12.5 |
| 10 | Magnesium phosphate + malic acid + buffering agent | 0.01-1.0 | 20-4000 | 50-500 | 3.5-12.5 |
| 11 | Magnesium acetate + oxalic acid + buffering agent | 0.01-1.0 | 10-1000 | 50-500 | 3.5-12.5 |
| 12 | Magnesium sulphate + ethylenediamine tetraacetic acid + buffering agent | 0.01-1.0 | 30-4000 | 50-500 | 3.5-12.5 |
| 13 | Magnesium gluconate + sodium hydroxide + buffering agent | 0.01-1.0 | 30-4000 | 50-500 | 3.5-12.5 |
| 14 | Magnesium hydroxide + phosphoric acid + buffering agent | 0.01-1.0 | 30-4000 | 50-500 | 3.5-12.5 |
| 15 | Magnesium iodate + acetic acid + buffering agent | 0.01-1.0 | 120-2000 | 50-500 | 3.5-12.5 |
| 16 | Magnesium chloride + oxalic acid + buffering agent | 0.01-1.0 | 50-1000 | 50-500 | 3.5-12.5 |

Table 2 shows quantitative indication of XPS analysis on atomic composition of a magnesium titanate oxide film formed on the implant surface by low voltage dielectric breakdown anodic oxidation in a magnesium-containing solution in accordance with Examples of the present invention.

TABLE 2

| Element | Sample 1 | Sample 2 | Sample 3 | Sample 4 | Sample 5 | Sample 6 |
|---|---|---|---|---|---|---|
| Ti | 18.78 | 26.29 | 5.72 | 6.4 | 6.51 | 7.32 |
| O | 55.72 | 56.22 | 69.23 | 67.35 | 56.32 | 50.07 |
| Mg | 1.84 | 2.25 | 13.6 | 15.23 | 25.58 | 32.31 |
| C | 15.24 | 9.57 | 9.44 | 7.02 | 7.32 | 6.38 |
| P | 5.86 | 3.1 | 0 | 1.4 | 0 | 2.4 |
| N | 1.4 | 2.02 | 0 | 0 | 0.6 | 1.2 |
| S | 0.3 | 0 | 0.5 | 0.5 | 0 | 0 |
| Na | 0.5 | 0.5 | 0 | 0 | 2.13 | 0.3 |
| K | 0 | 0 | 0 | 0.6 | 0 | 0 |
| Ca | 0 | 0 | 0 | 0 | 0.8 | 0 |

As can be seen from Table 2 above, magnesium titanate in accordance with the present invention contains 6 to 26% of titanium, 51 to 71% of oxygen and 1.8 to 32% of magnesium, as main ingredients, 6 to 15% of carbon, 0.3 to 6% of phosphorus, 0.3 to 2.1% of sodium and 1 to 2% of nitrogen, as minor ingredients, and sulfur, calcium and potassium in a small amount of less than 1%.

FIGS. 3 through 6 show results of a qualitative analysis of a magnesium titanate oxide film in accordance with the present invention, by XPS analysis. As can be seen from FIG. 4, magnesium shows chemical shifting from 1303.96 eV up to 1302.88 eV in binding energy at Mg 1 s. This means that the chemical binding state of the surface of the magnesium titanate oxide film varies depending upon elemental Mg content. Such results indicate that values of natural numbers x, y and z in the magnesium titanate oxide film may vary within a constant range.

Figure 7:
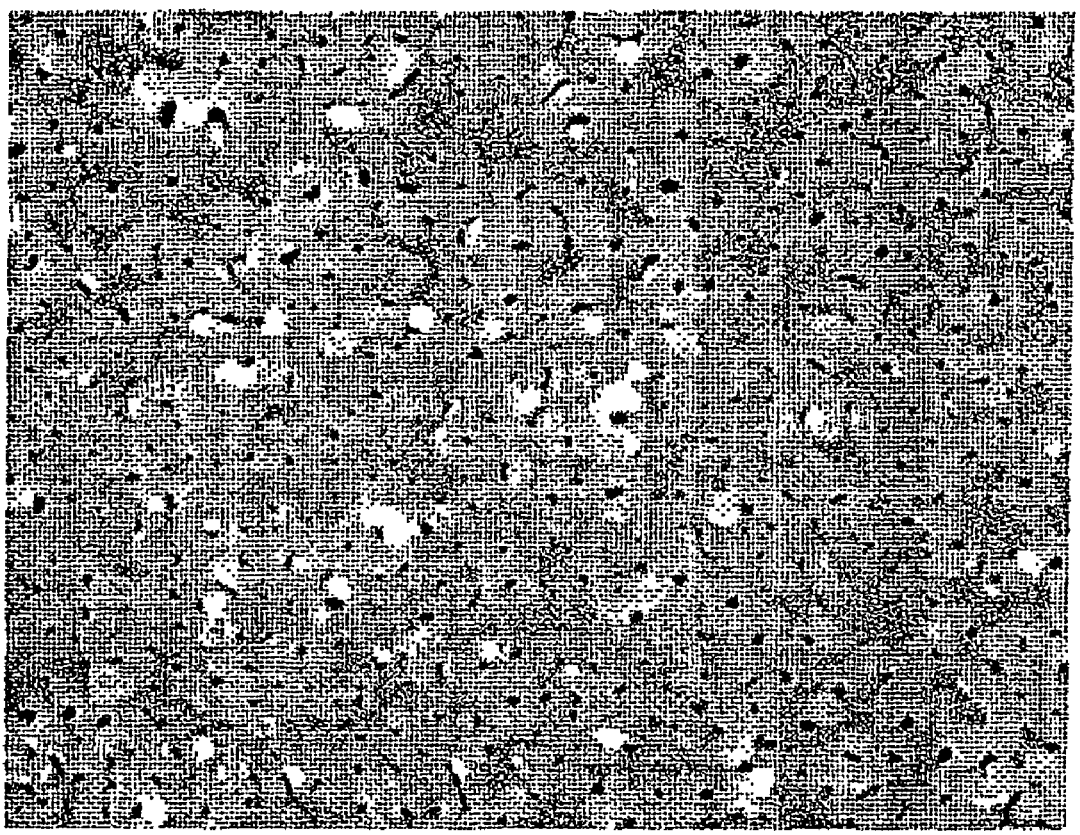
FIGS. 7 and 8 are, respectively, electron micrographs of the surface of a magnesium titanate oxide film in accordance with the present invention.
Figure 8:
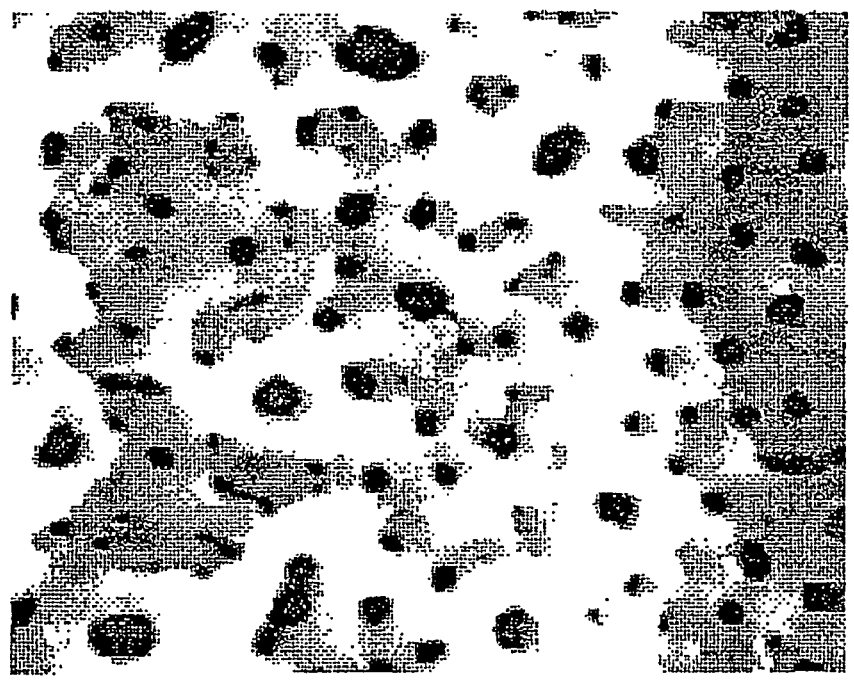
Figure 9:
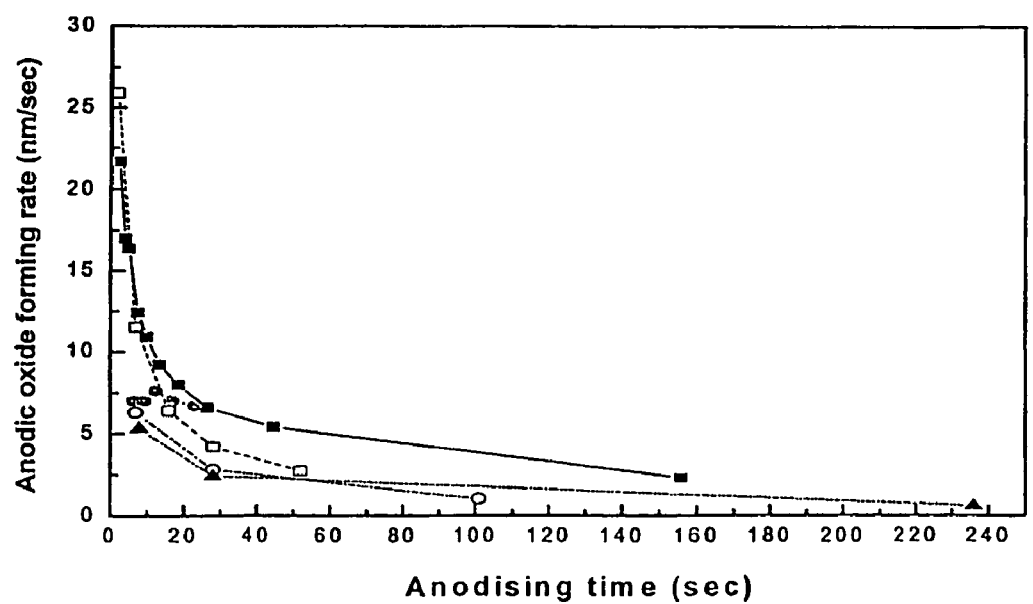
FIG. 9 is a graph showing a relationship between an increasing rate of a magnesium titanate oxide film in accordance with the present invention and time/voltage.
Figure 10:
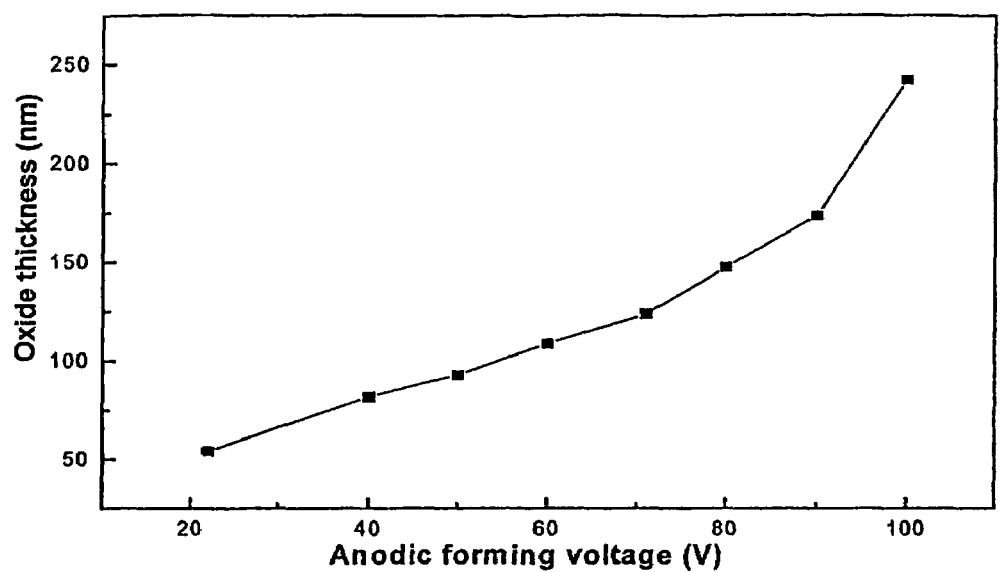
FIG. 10 is a graph showing a relationship between a thickness of a magnesium titanate oxide film in accordance with the present invention and voltage.

Next, varying the concentration of the electrolyte solution in the magnesium titanate oxide film imparts the following effects. Generally, in a curve showing voltage-to-time characteristics, higher concentrations of the electrolyte solution containing magnesium drop the formation rate of the magnesium titanate oxide film, and lowers dielectric breakdown voltage. Therefore, the higher the concentration of electrolyte solution containing magnesium became, the higher the amount of magnesium adsorbed into the titanium oxide film became, until the magnesium content reaches 32%. FIG. 7 is an electron micrograph of a surface of a magnesium titanate oxide film in the case of a lower concentration of the electrolyte solution, while FIG. 8 is an electron micrograph of a surface of a magnesium titanate oxide film in the case of a higher concentration of the electrolyte solution. As can be seen from FIGS. 7 and 8, the magnesium titanate oxide film formed in the higher concentration mixed solution has greater surface porosity, as compared to the magnesium titanate oxide film formed in the lower concentration mixed solution.

In accordance with Examples of the present invention, magnesium content in the magnesium titanate oxide film also varies depending on changes in current density. In general, when the current density increases up to 4000 mA/cm$^2$, a formation rate of the anodized film sharply increases, and as a result, the thickness of the film also increases. Further, increased current density of up to 4000 mA/cm$^2$ contributes to an increased pore size on the surface of the magnesium titanate oxide film, and increased surface porosity induces attachment of proteins and ingrowth of bone tissue into pores, thereby reinforcing mechanical binding with the implant.

Next, changes in voltage at which anodic oxidation on the magnesium titanate oxide film occurs provides the following results. The thickness of the magnesium titanate oxide film may increase up to several tens of micrometers proportional to a given voltage along with time. For example, in any solution given in Table 1, the thickness of the oxide film containing magnesium may grow up to 30 μm at a voltage of DC 500 V. Voltage for colloidal deposition of magnesium ions into the oxide film and simultaneously, formation of pores on the surface of the magnesium titanate oxide film is DC 60 V. Further, since the thicker oxide film leads to lower mechanical strength thereof (for example, tensile strength, compressive strength), there is a great risk of delamination of the oxide film into bone tissue from the interface between the implant and bone tissue. Therefore, dielectric breakdown voltage necessary for making the thickness of 300 nm to 20 µm, which is an optimum magnesium titanate oxide film thickness for successful osseointegration of the magnesium titanate oxide film implant, is 60 to 450 V. This is a preferred voltage range by which the generated pore size and porosity of the magnesium titanate surface exerts osseoinductive properties while meeting magnesium content of more than 5% in the magnesium titanate oxide film.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A process for preparing a magnesium titanate oxide film implant, comprising:
    irradiating UV light on an implant body made of titanium or a titanium alloy in distilled water for more than 2 hours;
    dipping the UV light-irradiated implant body in an electrolyte solution containing magnesium, the electrolyte solution having a concentration ranging from 0.01M to 1.0M; and
    coating a magnesium titanate oxide film on the dipped implant body by anodic oxidation at a voltage of 60 to 500V.

2. The process as set forth in claim 1, wherein the electrolyte solution is a single or mixed solution containing magnesium.

3. The process as set forth in claim 1, wherein the electrolyte solution has a pH of 3.0 to 12.5.

4. The process as set forth in claim 1, wherein the current density for performing the anodic oxidation is within the range of 30 to 4000 mA/cm$^2$.

5. The process as set forth in claim 2, wherein the electrolyte solution has a pH of 3.0 to 12.5.

6. The process as set forth in claim 2, wherein the current density for performing the anodic oxidation is within the range of 30 to 4000 mA/cm$^2$.

7. A process for preparing a magnesium titanate oxide film implant comprising:
    irradiating UV light on the implant body made of titanium or a titanium alloy in distilled water for more than two hours;
    dipping the UV light-irradiated implant body in an electrolyte solution containing magnesium, having a pH of between 3.0 to 12.5 and a concentration ranging between 0.01M to 1.0M; and
    coating a magnesium titanate oxide film on the dipped implant body by anodic oxidation within a range of between 30 mA/cm$^2$ and 4000 mA/cm$^2$, at a voltage of between 60V to 500V to prepare the magnesium titanate implant comprising the implant body containing said titanium or said titanium alloy, and the magnesium titanate oxide film formed on the surface of the said implant body, the magnesium titanate oxide film comprising an upper porous layer and a lower barrier layer.

* * * * *